United States Patent [19]

Imaizumi et al.

[11] Patent Number: 4,810,780

[45] Date of Patent: Mar. 7, 1989

[54] PROTEIN HAVING PHOSPHOLIPASE A2 INHIBITORY ACTIVITY

[75] Inventors: Atsushi Imaizumi; Takashi Kamimura; Yorimasa Suwa; Masahiro Okada, all of Tokyo, Japan

[73] Assignee: Teijin Limited, Osaka, Japan

[21] Appl. No.: 903,549

[22] Filed: Sep. 4, 1986

[30] Foreign Application Priority Data

Sep. 4, 1985 [JP] Japan ................... 60-193699

[51] Int. Cl.$^4$ ............................................. A61K 37/64
[52] U.S. Cl. .................................. 530/350; 530/395; 530/848; 530/324
[58] Field of Search ............... 530/350, 324, 300, 352, 530/395, 848

[56] References Cited

U.S. PATENT DOCUMENTS 4,402,872 9/1983 Bohn .................................. 530/369

OTHER PUBLICATIONS

Flower et al., "Anti-Inflammatory Steroids Induce Biosynthesis of a Phospholipase A$_2$ Inhibitor which Prevents Prostaglandin Generation" Nature, vol. 278, pp. 456–459.
Blackwell et al., "Macrocorton: A Polypeptide Causing the Anti-Phospholipase Effect of Gluco-Corticoids" Nature, vol. 287, Sep. 11, 1980, pp. 147–149.
Wallner et al., "Cloning and Expression of Human Lipocortin, a Phospholipase A$_2$ Inhibitor with Potential Anti-Inflammatory Activity" Nature, vol. 320, Mar. 6, 1986, pp 20 and 77–81.
Rothhut et al., "Further Characterization of the Glucocorticoid-Induced Antiphospholipase Protein 'Renocortin'" Biochem Biophyl Res Comm, vol. 117, No. 3, 1983, pp. 878–884.
Hirata et al., "A Phospholipase A$_2$ Inhibitory Protein in Rabbit Neutrophils Induced by Glucocorticoids" Proc Nat'l Acad Sci, USA, vol. 77, No. 5, pp. 2533–2536, May 1980.
DiRosa et al., "Nomenclature Announcement–Anti-Phospholipase Proteins" VIth International Conference on Prostaglandins, Oct., 1984, vol. 28, No. 4, pp. 440–443.
Pepinsky et al., "Purification and Partial Sequence Analysis of a 37-kDa Protein That Inhibits Phospholipase A$_2$ Activity From Rat Peritoneal Exudates" J. Biol. Chem., vol. 261, No. 9, Mar. 25, pp. 4239–4246, 1986.

Primary Examiner—John Kight
Assistant Examiner—Nathan M. Nutter
Attorney, Agent, or Firm—Sughrue, Mion, Zinn, Macpeak & Seas

[57] ABSTRACT

Protein having a phospholipase A$_2$ inhibitory activity which has the nature to be induced from cells upon administration of glucocorticoid and has a phospholipase A$_2$ inhibitory activity.

1 Claim, 4 Drawing Sheets

PROTEIN HAVING PHOSPHOLIPASE A2 INHIBITORY ACTIVITY

FIELD OF THE INVENTION

The present invention relates to protein having a phospholipase Az (PLA$_2$) inhibitory activity. More particularly, this invention relates to protein induced from cells by the administration of glucocorticoid to have a PLA$_2$ inhibitory activity.

BACKGROUND ART

Glucocorticoid is now widely used as one of the most efficacious medicines against various inflammatory diseases and allergic diseases inclusive of chronic articular rheumatism, lupus erythematosus, and bronchial asthma. The mechanism of its action is attributable to the anti-inflammatory action, anti-edematous action, and immunosuppresive action of glucocorticoid. Of these actions, the mode of anti-inflammatory action relates to the inhibition of the release of arachidonic acid, which is the precursor of prostaglandins or leukotriens regarded to be inflammatory mediators. A new theory has recently been put forward by Flower (Nature 278: 456 (1979)) to the effect that glucocorticoid suppresses the activity of PLA$_2$ which is a key enzyme to release arachidonic acid directly from the phospholipid. With regard to the mode of action taken by glucocorticoid, it is understood that, upon entering into a cell, glucocorticoid is first bound to the receptor of the cell, and the resulting complex is translocated into the nucleus to activate the specific gene, finally inducing the synthesis of specific protein. Actually, Tsurufuji et al. have shown (in Nature 280: 408 (1979)) that cycloheximide, inhibitor of protein synthesis, and actinomycin D, inhibitor of m RNA synthesis, suppress the therapeutic effect of glucocorticoid against paw edema (experimental animal model of inflammation) caused by serotonin. It is, therefore, sugestive from the abovementioned results that glucocorticoid displays its anti-inflammatory activity through the induction of the synthesis of PLA$_2$ inhibitory protein.

Attempts have hitherto been made by several groups to isolate such a protein whose synthesis is induced by glucocorticoid and that inhibits the activity of PLA$_2$ in vitro and suppresses the production of prostaglandin in vivo; however, none of these trials have succeeded in purifying a protein, deducing even a part of its primary structure by protein microsequence analysis, clarifying the composition of amino acid, and, above all, isolating a protein which definitely displays the PLA$_2$ inhibitory activity.

DISCLOSURE OF THE INVENTION

The present inventors have conducted intensive researches on the isolation and purification of proteins which are induced from cells by glucocorticoid treatment and specifically inhibit the PLA$_2$ activity with the purpose of clarifying the mechanism of action taken by steroid through the research on the subject proteins, with the result of achieving the present invention.

The present invention relates to a protein which has the PLA$_2$ inhibitory activity, particularly which by nature is induced from a cell by administration of glucocorticoid such as dexamethasone and it is especially desirable to have one whose amino acid composition (mole is as follows: aspartic acid (Asp) 12.3, threonine (Thr) 5.1, serin (Ser) 4.8, glutamic acid (Glu) 20.3, glycine (Gly) 4.3, alanine (Ala) 6.5, valine (Val) 6.8, $\frac{1}{2}$-cystine ($\frac{1}{2}$-Cys) 0.4, methionine (Met) 3.2, isoleucine (ILe) 2.1, leucine (Leu) 11.9, tyrosin (Tyr) 1.4, phenylalanine (Phe) 3.4, lysine (Lys) 7.7, histidine (His) 1.6, arginine (Arg) 3.8, proline (Pro) 4.0, and tryptophane (Trp) 0.4. Also, the protein according to the present invention, of rat origin, with a molecular weight of about 43,000 determined by gel filtration, is purified from the exudate collected in the rat peritoneal cavity and gives a single band both under the nonreductive and reductive conditions in SDS-polyacrylamide gel electrophoresis. This is an acid protein which is water soluble and is not inactivated in a solution of low pH value and in the presence of an organic solvent and is endowed with a PLA$_2$ inhibitory activity, and whose 26 amino acids from the N terminal consist of NH$_2$-Glu-Val-Thr-Ser-Asp-Gln-Val-Ala-Asn-Val-Met-Trp-Asp-Tyr-Phe-Thr-Gln-Leu-Ser-Asn-Asn-Ala-Lys-Glu-Ala-Val.

BRIEF DESCRIPTION OF THE DRAWINGS

FIG. 7 shows an elution pattern of the subject protein obtained by reverse-phase HPLC with a low acetonitrile concentration gradient.

BEST MODE FOR CARRYING OUT THE INVENTION

Figure 1:
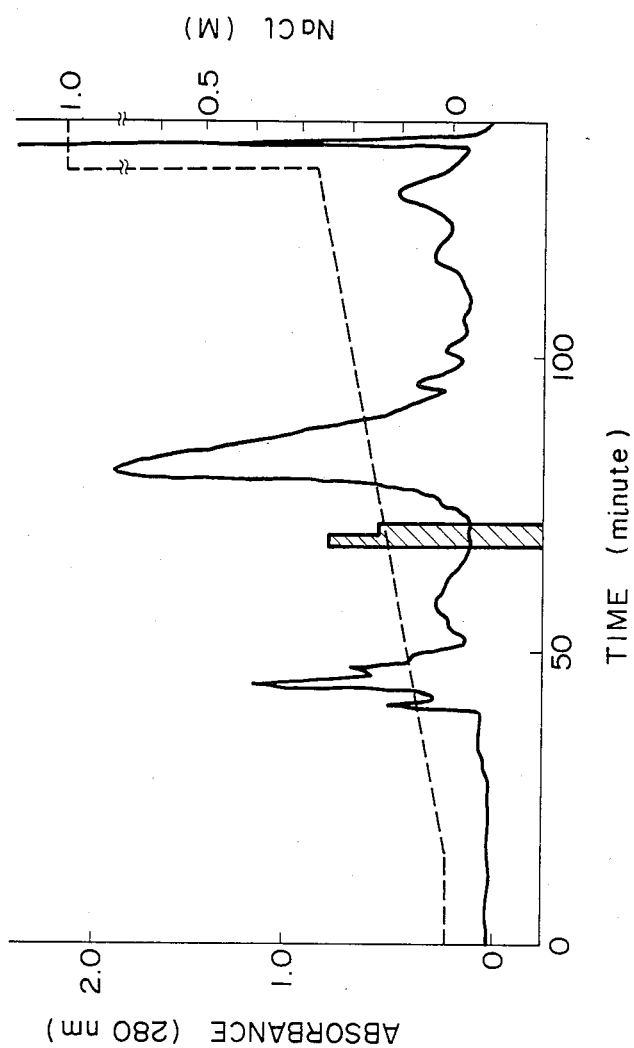
FIG. 1 shows an elution pattern of the subject protein obtained by anion-exchange HPLC.

Reference may here be made as to the system of evaluation which forms an important part in the course of working out the present invention. It has hitherto been known that, in the evaluation of phospholipase activity, the reactivity of phospholipase, being an enzyme itself, is profoundly influenced by the state of substrate (phospholipid) in the aqueous solution. Only a small degree of activity is displayed when the monomer substrate is in the dispersed state while a high level of activity is displayed when the substrate is in the state of enough micelle concentration. Therefore, it is necessary to keep phosphatidyl choline, which makes the substrate, in a micellar state. To achieve such object, there is a known practice to add various kinds of surface-active agents to the reaction system. It is known that CTAB (cetyl trimethylammonium bromide), which is a surface-active agent of cation type, suppresses PLA$_2$ activity at such a low concentration as 0.01%, that SDS (sodium dodecyl sulfate), which is a surface-active agent of anion type, shows no suppressive activity at 0.01% concentration but displays about 26% suppressibility at 0.1% concentration, and that, in case of a nonionic surface-active agent, addition of 0.1% agent to the reaction system shows no PLA$_2$ inhibitory activity (T. Teramoto et al., 1983. J. Biochem. 93, 1353).

On the other hand, it is necessary to establish a reaction system which will not spoil the affinity for phospholipase in order to obtain a protein which specifically inhibits PLA$_2$ and since the addition of a detergent in excess damages the affinity of PLA$_2$ for the desired protein, such use of surface-active agents is not suited for the system of evaluation of the desired protein.

Based on the above-mentioned knowledge, the present inventors have established a reaction system (inclusive of nonionic detergent and an appropriate amount of Ca$^{2+}$ ion system) in which the substrate is kept in a micellar state and the affinity between PLA$_2$ and the intended protein is not damaged, and completed the present invention by use of such reaction system.

The description will next be made as to the method of isolating and purifying the protein of this invention. The method of induction of the subject protein include the direct administration of steroid in vivo and in vitro induction using a normal cell or an established cell line to directly contact with steroid. The example, rats were injected subcutaneously on the back with dexamethasone. One and half hour after injection, the rats were sacrified by carbon dioxide and the peritoneal cavities were rinsed thoroughly with saline containg heparin and PMSF (phenylmethylsulphonylfluoride). The lavages were recovered, combined, dialyzed essentially against an ammonium acetate buffer, and lyophilized. About 20 mg of crude frozen sample of rat peritoneal lavage per head was obtained. The subject protein was isolated and purified from thus obtained sample used as a starting material according to a process mentioned below, for instance. The samples were applied to anion-exchange HPLC and PLA$_2$ inhibitory fraction was obtained. These active fraction were found with mixtures of various proteins by SDS-polyacrylamide gel electrophoresis and further purification carried out by gel filtration and reverse-phase HPLC. The obtained active fraction was shown single band in SDS-polyacrylamide gel electrophoresis. About 50 μg of PLA$_2$ inhibitory proteins were isolated from about 200 mg of the sample. The properties of thus obtained proteins: molecular weight of about 43,000; water soluble, active at low pH. Therefore it proved to be acid proteins. Sequence analysis showed that N terminal of subject proteins consisting of NH$_2$-Glu-Val-Thr-Ser-Asp-Gln-Val-Ala-Asp-Val-Met-Trp-Asp-Tyr-Phe-Thr-Gln-Leu-Ser-Asn-Asn-Ala-Lys-Glu-Ala-Val. The foregoing explanation mainly covers a mode of processes for isolating and purifying the PLA$_2$ inhibitory active proteins of this invention from the steroid induced rat peritoneal exudates; however, no limit shall be placed upon the sources of proteins and processes for their production in the present invention. They may be extracted, isolated, and purified from human beings and other animals or furthermore they may be produced from microorganisms or animal cells by means of genetic engineering. So far as they are proteins having a PLA$_2$ inhibitory activity, they are involved in the present invention.

Based on the 26-amino acid sequence from N-terminal of the subject protein, searches for known proteins having the homology with such an arrangement have been made. The result of such searches is the finding that rat apolipoprotein A IV has a 26-amino acid from N terminal wholly homologous with that of the subject protein.

Various methods of testing and determination used in this invention are as follows.

(1) Method for determining PLA$_2$ inhibitory activity:

260 μl of the sample or a control (20 mM Tris-15 mM NaCl) and 10 μl of 0.1% Triton X-100 and 10 μl of 150 mM CaCl$_2$ were mixed with 10 μl of PLA$_2$ (Porcine pancreas; produced by Sigma Co., 100 ng in absolute amount) to make a standard reaction system, which was then incubated at 37° C. with moderate shaking for 1.5 hours. Then 10 μof L-3-phosphatidylcholine, 1-stearoyl-2-[1-$^{14}$C] arachidonyl (final concentration 0.72 μM-12.5 μCi) was added thereto and the incubation was continued at 37° C. for 5 minutes. Thereafter, the reaction was terminated by use of Dole's reagent and $^{14}$C-arachidonic acid was extracted with heptane and the determination was then made with the liquid scintillation counter.

(2) SDS-polyacrylamide gel electrophoresis:

Part of the sample fractionated by means of various chromatographical methods was heated at 100° C. in the presence of 1% SDS, 2-mercaptoethanol for 10 minutes. Then the sample was electrophoresed in 12.5% polyacrylamide gel for 1.5 hours at 15 mA. After the electrophoresis was over, the sample was stained with use of silver stain kit (Bio-Rad ®).

(3) Method for determining the primary structure of protein:

The determination was performed with the use of a gas phase protein sequencer (manufac. by Applied Biosystem, model 470 A). 10 μg of the isolated and refined sample was dissolved in 30 μl of 1% SDS and was applied to the gas phase protein sequencer. PTH (phenylthiohydantoin) amino acid derivatives which had been antomatically made to undergo Edman's decomposition were then analyzed as the respective amino acids by means of HPLC.

(4) Analysis of the primary structure of protein:

Along with the determination of the primary structure of the subject protein, research was made as to its sequential homology in comparison with that of known proteins. As the data base for the primary structure, the data collected by Protein Research Foundation (476 Ina Minoh-shi, Osaka 562, JAPAN) and compiled into the data base (trade name "Prinas") by Mitsui Knowledge Industry Co., Ltd. was used.

The present invention is described in detail by the following examples.

EXAMPLE 1

(1) Preparation of crude sample of rat peritoneal lavages

Fifty male, 8-week-old SD rats were injected subcutaneously on the back with 1.5 mg/kg of dexamethasone and 1.5 hours later they were sacrificed by carbon dioxide and the peritoneal cavities were rinsed thoroughly with 12 ml per rat of saline containing 2 units/ml heparin and 50 μM PMSF (phenylmethylsulphonylfluoride) and about 500 ml of lavages were collected. The lavages were dialyzed twice against 10 mM ammonium acetate buffer (pH 7.4) in amount of 40 times and lyophilized to obtain about 940 mg of a crude frozen sample of rat peritoneal lavages.

(2) Isolation and purification of subject protein by anion-exchange HPLC

While being cooled on ice, 200 mg of a crude frozen sample of rat peritoneal lavages were dissolved in 50 m( of 20 mM Tris-HCl (pH 8.0). After the solution was filtered through a 0.45 μm membrane filter, the filtrate was directly applied to a column (of TSK Gel DEAE-5PW) with the use of an sp 8750 HPLC pump. The adsorbed sample was eluted at a flow rate of 2.5 ml/min. with an NaCl linear gradient as shown with a broken line in FIG. 1. In FIG. 1, a solid line indicates the amount of proteins monitored by absorbance at UV 280 nm and a strong PLA$_2$ inhibitory activity was detected in the fractions (No. 35, No. 36) preceding the large protein peak (a diagonal shaded area in FIG. 1). When fractions No. 35 and No. 36 were subjected to SDS electrophoresis, it was found that these fractions were mixtures of proteins (18, 43, 50, 60K).

(3) Isolation and purification of the subject protein by gel filtration HPLC

Figure 2:
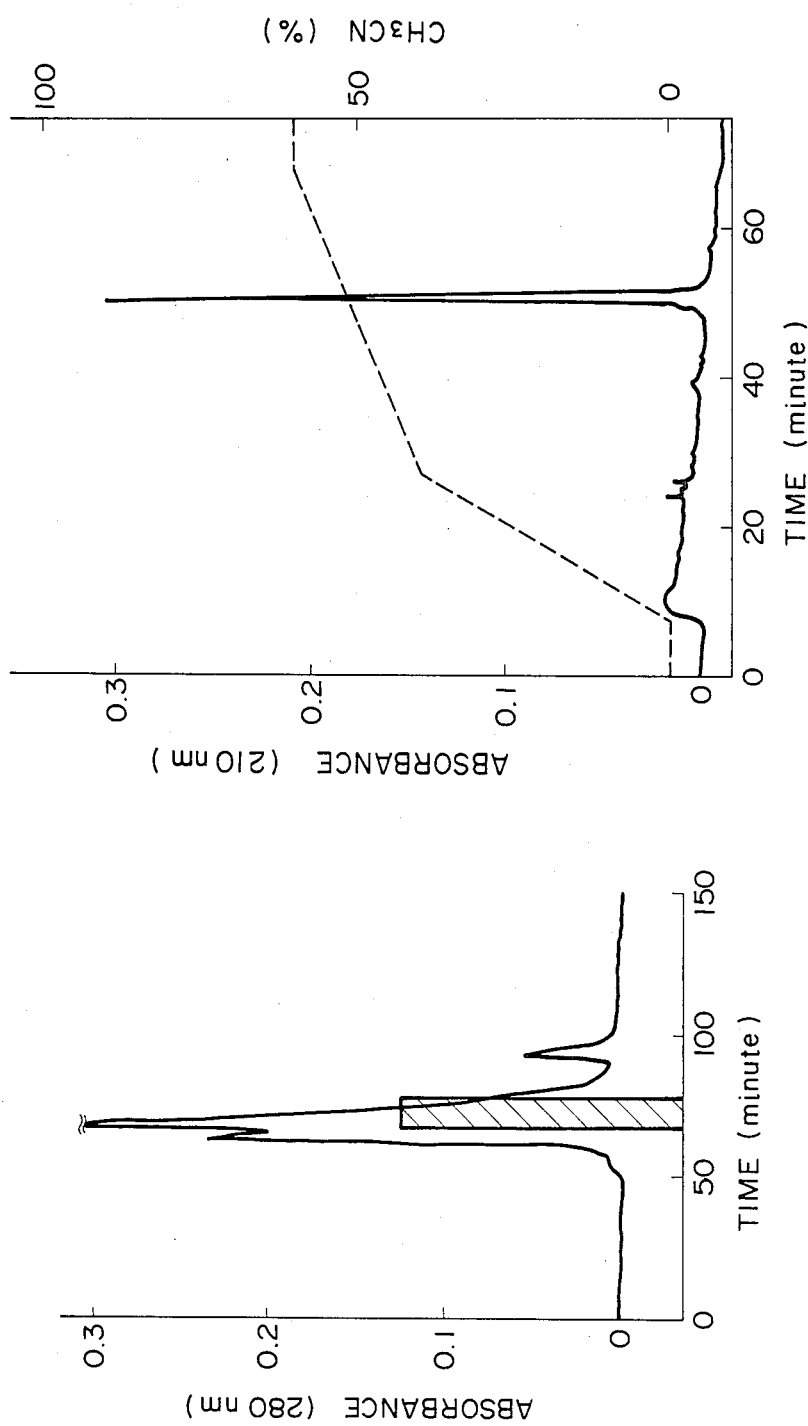
FIG. 2 shows an elution pattern of the subject protein obtained by gel filtration HPLC.

Furthermore, to purify the PLA$_2$ inhibitory fractions (No. 35, No. 36), the fractions were concentrated by use of Centricon-10. The fractions which were concentrated to 0.7 ml were applied to a gel filtration column (TSK Gel G3000 SW) equilibrated with 20 mM Tris-15 mM NaCl (pH 7.4) and eluted at a flow rate of 0.2 ml/min. The result is shown in FIG. 2, which indicates the detection of a strong PLA$_2$ inhibitory activity in the fractions, No.8 ~ No.10 (a diagonal shaded area in FIG. 2). The analysis of these fractions by SDS polyacrylamide gel (SDS-PAGE) electrophoresis showed that there was no 18K protein in them but there were still 43K and 60K proteins in these fractions.

Figure 3:
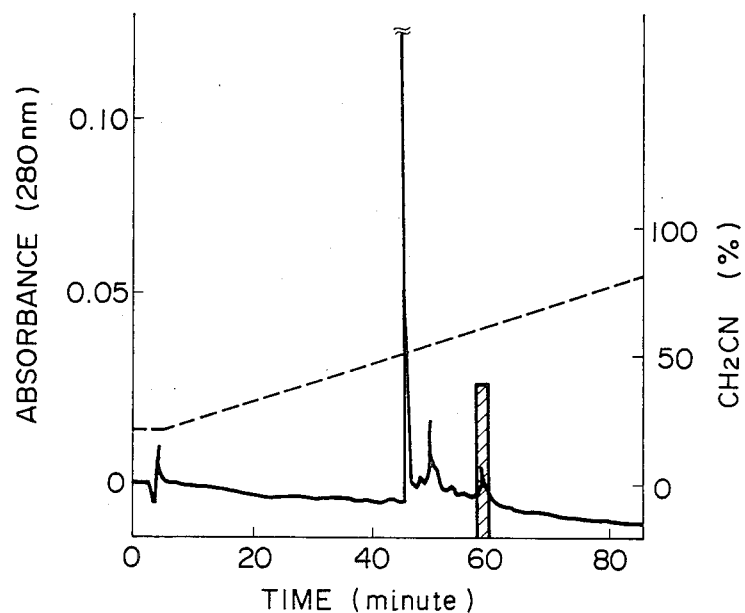
FIG. 3 shows an elution pattern of the subject protein obtained by reverse-phase HPLC.

(4) Separation and purification of the subject protein by reverse-phase HPLC 1.0 ml of the fraction (No. 10) whose PLA$_2$ inhibitory activity was detected by gel filtration HPLC was applied to a column (Bio-Rad, Hi-Pore RP-304) equilibrated with 0.1% TFA and eluted at a flow-rate 1.0 ml/min with an acetonitrile linear gradient as shown with a broken line in FIG. 3. The fractions, whose absorbance was detected at UV 280 nm, were dialyzed against 20 mM Tris-150 mM NaCl (pH 8.0) and had their PLA$_2$ inhibitory activity determined. As the result of such determination, a remarkable PLA$_2$ inhibitory activity was detected in No. 32 fraction as shown in FIG. 3. When this fraction was subjected to SDS-PAGE, it was found that the protein was single, with a molecular weight of about 43,000.

EXAMPLE 2

A further example is shown below, wherein the intended protein was isolated and purified according to another method of isolation, and purification from a crude frozen sample of rat peritoneal cavity lavages, a starting material, obtained from 50 male, 8-week-old SD rats injected with dexamethasone in the same way as Example 1.

Figure 4:
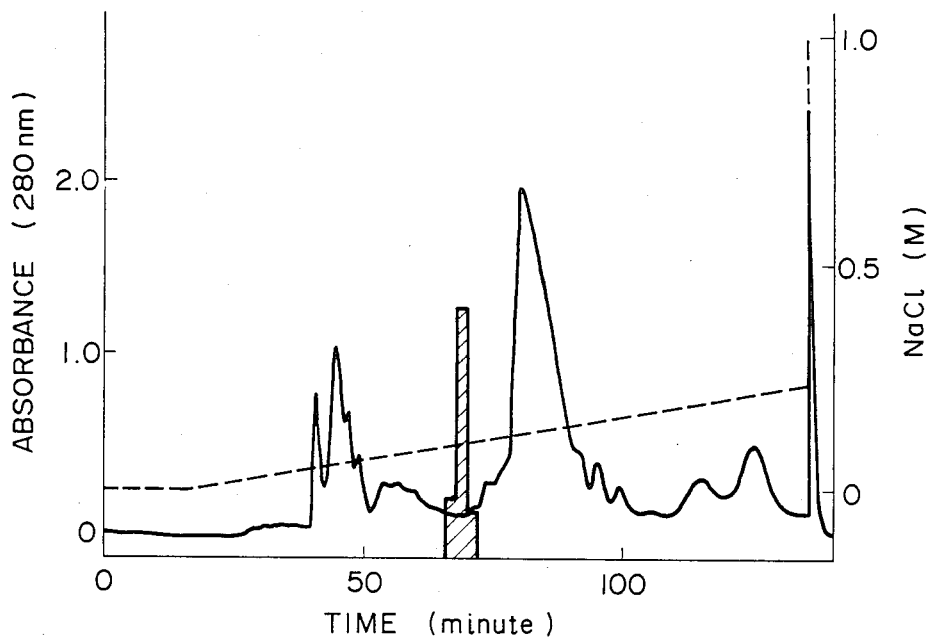
FIG. 4 shows an elution pattern of the subject protein obtained by anion-exchange HPLC.
Figure 5:
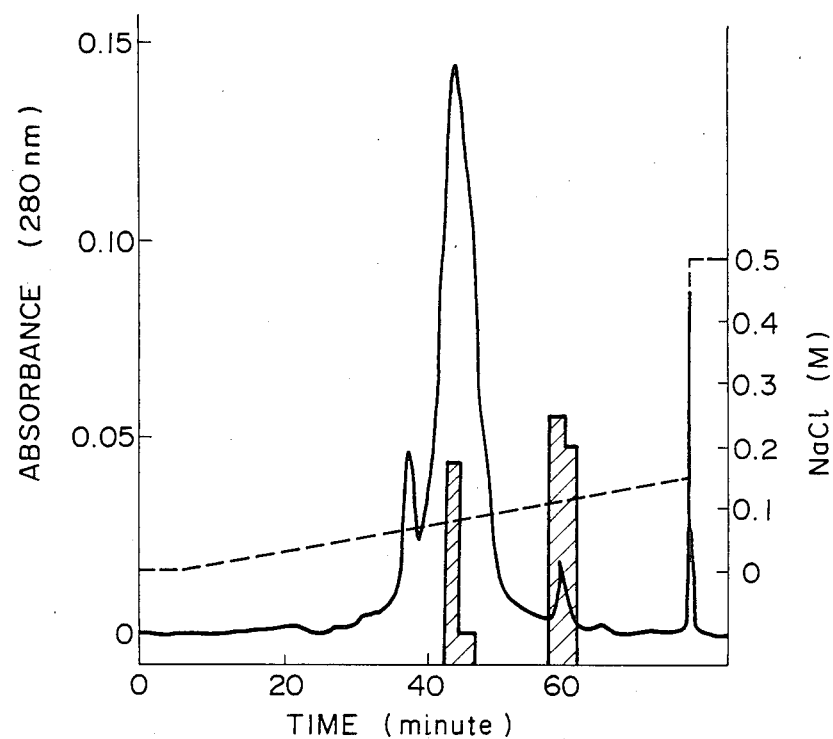
FIG. 5 shows an elution pattern of the subject protein obtained by anion-exchange HPLC with a low NaCl concentration gradient.
Figure 6:
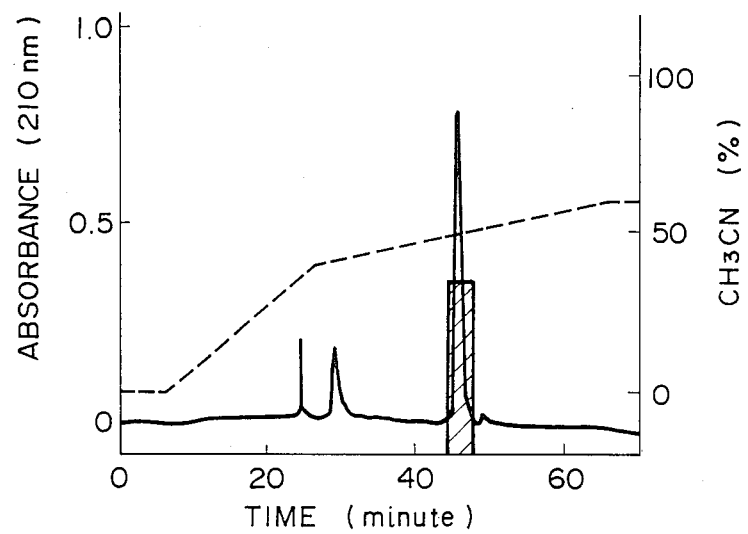
FIG. 6 shows an elution pattern of the subject protein obtained by reverse-phase HPLC.

While cooling on ice, about 200 mg of the starting material was dissolved in 50 ml of 20 mM Tris-HCl, and the solution was filtered through a 0.45 μm-membrane filter and was then directly applied to anion-exchange HPLC on a column of TSK gel DEAE-5 PW by use of an sp 8750 HPLC pump, and was eluted with an NaCl linear gradient shown with a broken line in FIG. 4 to obtain a PLA$_2$ inhibitory fraction (a diagonal shaded area in FIG. 4). The obtained fraction was rechromatographed in the same way as above and was purified with an NaCl linear gradient as shown with a broken line in FIG. 5. As shown in FIG. 5, PLA$_2$ inhibitory activity (diagonal shaded areas in FIG. 5) was detected at a point of 41 to 44 minutes and another point of 56 to 59 minutes in elution time. The latter activity peak was further subjected to reverse-phase HPLC. To say more exactly, said active fraction was applied to a column (Bio-Rad Hi-Pore RP 304) equilibrated with 0.1% TFA and was eluted at a flow rate of 1.0 ml/min with an acetonitrile linear gradient shown by a broken line in FIG. 6. As shown in FIG. 6, 3 protein peaks were obtained and the major peak was found to have a PLA$_2$ inhibitory activity (a diagonal shaded area in FIG. 6).

With the object of further purifying the active fraction, it was subjected to reverse-phase HPLC with a modified acetonitrile linear gradient. As the result of such chromatography, one activity peak as shown in FIG. 7 was obtained. This peak was further electrophoresed in SDS and found to be consisted of single proteins having molecular weight of about 43,000.

EXAMPLE 3

The primary structures of proteins obtained from the samples which had been isolated and purified respectively in Example 1 and Example 2 were partially determined. The result showed that both proteins had the same sequence of amino acids from the N terminal. The partial sequence of amino acids from the N terminal was as follows: NH$_2$-Glu-Val-Thr-Ser-Asp-Gln-Val-Ala-Asn-Val-Met-Trp-Asp-Tyr-Phe-Thr-Gln-leu-Ser-Asn-Asn-Ala-Lys-glu-Ala-Val.

What is claimed is:

1. Protein having a phospholipase A$_2$ inhibitory activity wherein the constituent amino acid of said protein has a composition (mole %) consisting of aspartic acid (Asp) 12.3, threonine (Thr) 5.1, serine (Ser) 4.8, glutamic acid (Glu) 20.3, glycine (Gly) 4.3, alanine (Ala) 6.5, valine (Val) 6.8, ½-cystine (½-Cys) 0.4, methionine (Met) 3.2, isoleucine (Ile) 2.1, leucine (Leu) 11.9, tyrosine (Tyr) 1.4, phenylalanine (Phe) 3.4, lysine (Lys) 7.7, histidine (His) 1.6, arginine (Arg) 3.8 proline (Pro) 4.0, and tryptophane (Trp) 0.4 and wherein said protein is one removed from the abdominal cavity of a rat after the administration of glucocorticoid and purified, with a molecular weight of about 43,000, and whose 26 amino acids from the N terminal consist of NH$_2$-Glu-Val-Thr-Ser-Asp-Gln-Val-Ala-Asn-Val-Met-Trp-Asp-Tyr-Phe-Thr-Gln-Leu-Ser-Asn-Asn-Ala-Lys-Glu-Ala-Val.

* * * * *